United States Patent [19]

Dohi et al.

[11] Patent Number: 5,565,317
[45] Date of Patent: Oct. 15, 1996

[54] PERFUSION AND STORAGE SOLUTION CONTAINING SODIUM LACTOBIONATE, SODIUM DIHYDROGENPHOSPHATE, RAFFINOSE, GLUTATHIONE, ALLOPURINOL AND NAFAMOSTAT MESYLATE

[75] Inventors: Kiyohiko Dohi; Takashi Urushihara, both of Hiroshima; Masanori Iwata, Chiba, all of Japan

[73] Assignee: Torii Pharmaceutical Co., Ltd., Tokyo, Japan

[21] Appl. No.: 347,490

[22] PCT Filed: Feb. 23, 1993

[86] PCT No.: PCT/JP93/00219

§ 371 Date: Dec. 6, 1994

§ 102(e) Date: Dec. 6, 1994

[87] PCT Pub. No.: WO94/00008

PCT Pub. Date: Jan. 6, 1994

[30] Foreign Application Priority Data

Jun. 26, 1992 [JP] Japan ................................. 4-168977

[51] Int. Cl.⁶ ............................. A01N 1/02; A01N 43/04; A61M 1/00
[52] U.S. Cl. ............................. 435/1.2; 514/61; 514/832; 604/27
[58] Field of Search ................ 435/1, 1.2; 514/61, 514/832; 604/27

[56] References Cited

U.S. PATENT DOCUMENTS

| | | | |
|---|---|---|---|
| 4,798,824 | 1/1989 | Belzer et al. | 514/60 |
| 4,873,230 | 10/1989 | Belzer et al. | 514/60 |
| 4,879,283 | 11/1989 | Belzer et al. | 514/60 |
| 4,889,634 | 12/1989 | El-Rashidy | 210/646 |
| 4,938,961 | 7/1990 | Collins et al. | 424/606 |
| 5,145,771 | 9/1992 | Lemasters et al. | 435/1 |

FOREIGN PATENT DOCUMENTS

| | | |
|---|---|---|
| 62-0219235 | 9/1987 | Japan. |
| 1-246201 | 10/1989 | Japan. |
| 3-188001 | 8/1991 | Japan. |
| 4-128201 | 4/1992 | Japan. |

OTHER PUBLICATIONS

Tsuyoshi Morimoto, "An Experimental Study On Futhan In Pancreas Transplantation", Shinryo to Shinyaku (Clinic and New Drugs), vol. 29, No. 1, pp. 194–197 (1992).

Yoshifumi Naka et al., "Prevention of Pulmonary Edema in Autoperfusing Heart–Lung Preparation by FUT–175 and Leukocyte Depletion" *Transplantation Proceedings*, vol. XXI, No. 1, Feb. 1989 pp. 1353–1356.

Takashi Urushihara et al., "Efficacy of Futhan Rinse Solution following Rat Heart Preservation" *Chemical Abstracts*, vol. 119, No. 1, 5 Jul. 1993, Columbus, Ohio, US; abstract no. 4342 & Nippon Geka Gakkai Zasshi, vol. 93, No. 12, 1 Dec. 1992 p. 1514.

N. Harada et al. "Effect of Fosfomycin Fosmicin On Experimental Acute Pancreatitis Induced by Deoxycholic Acid in Rats" *Biological Abstracts*, vol. 91, Philadelphia, PA, US; abstract no. 106059.

Harada N. et al., "Stabilization of Glutathione–Containing Compositions with Gamma Cyclodextrin" *Chemical Abstracts*: 111:132914(1989).

Miyagawa S et al, Transplant Proc 24(2): 483–484 (Apr. 1992).

*Primary Examiner*—David M. Naff
*Assistant Examiner*—S. Saucier
*Attorney, Agent, or Firm*—Beveridge, DeGrandi, Weilacher & Young, L.L.P.

[57] ABSTRACT

A solution for the preservation or perfusion of organs contains sodium lactobionate, sodium dihydrogenphosphate, raffinose, glutathione, allopurinol, nafamostat mesilate (mesylate) and optionally cyclodextrin, preferably 100–120 mM, 2–25 mM, 25–35 mM, 2–4 mM, 1–2 mM and 0.5–1 mM, respectively. The solution may be used for perfusion and storage of organs. Also disclosed are methods of use of the solution to perfuse and store organs.

17 Claims, No Drawings

PERFUSION AND STORAGE SOLUTION CONTAINING SODIUM LACTOBIONATE, SODIUM DIHYDROGENPHOSPHATE, RAFFINOSE, GLUTATHIONE, ALLOPURINOL AND NAFAMOSTAT MESYLATE

The present invention relates to a solution for the preservation of organ or perfusate to be used when an organ is extirpated.

The drastic improvement of performance record of organ transplantation is attributable to the progress of organ storage solution or perfusate as well as the progress of surgical operations and the advancement of antibiotics and immunosuppressants.

In organ transplantation, perfusion of the transplanted organ is essential, but when perfusing the organ which is in an ischemic state, ischemic perfusion trouble is unavoidable. Thus, minimization of the cellular trouble caused in the process of perfusion is a key factor for the success of organ transplantation.

Hitherto, UW solution (JP-A-1-246201; a solution composed of potassium lactobionate, potassium dihydrogenphosphate, magnesium sulfate, sodium hydroxide, raffinose, adenosine, glutathione, insulin, bactrim, dexamethasone, allopurinol and hydroxyl ethyl starch) has been used as the storage solution, and Ringer's solution or Carolina Rinse solution (a solution composed of sodium chloride, potassium chloride, calcium chloride, sodium lactate, adenosine, allopurinol, desferrioxamine and glutathione) has been used as the perfusate. Further, the modified versions of these solutions featuring incorporation of proteinase inhibitors such as nafamostat mesilate in the compositions have been reported Shinryo to Shinyaku, *Clinic and New Drugs*, 29:194–197 (1992).

Of these organ storage solutions and perfusates, UW solution was developed by Belzer et al in 1987 and has phenomenally prolonged the organ preservable period. However, since this solution contains hydroxyl ethyl starch as noted from its composition, the solution is increased in viscosity in use, making it difficult to remove blood from the organ. Also, because of high potassium concentration, this solution gives detrimental effect to the vascular endothelium. This solution is also unsatisfactory in its buffering action. Further, it is costly as it contains insulin.

The organ preservable period of Ringer's solution or Carolina Rinse solution is 24 hours at most. This is rather unsatisfactory for a storage solution.

The object of the present invention is to provide an organ storage solution or perfusate at a low cost which is designed to safely preserve the organ to be transplanted or to protect the organ from cellular trouble caused in the process of perfusion.

The present inventors have tried to incorporate electrolyte, osmotic pressure regulator, proteinase inhibitor, etc., in various combinations in the storage solution or perfusate compositions and, as a result, completed the present invention to attain the desired end.

The organ storage solution or perfusate of the present invention comprises sodium lactobionate, sodium dihydrogenphosphate, raffinose, glutathione, allopurinol and nafamostat mesilate. The especially preferred organ storage solution or perfusate of the present invention is characterized by having the composition of 100–120 mM sodium lactobionate, 25–35 mM sodium dihydrogenphosphate, 25–35 mM raffinose, 2–4 mM glutathione, 1–2 mM allopurinol and 0.5–1 mM nafamostat mesilate, an osmotic pressure of 290–350 mOsm/l and a pH of 7.0–8.0.

Further, in the formulation of the present invention, in order to prevent the precipitation caused by compositional interaction, it is desirable to add an appropriate amount of cyclodextrin. As cyclodextrin, α-cyclodextrin, β-cyclodextrin or γ-cyclodextrin may be used singly, or a mixture of two or more of said types of cyclodextrin may be used.

Thus, the present invention further relates to an organ storage solution or perfusate comprising sodium lactobionate, sodium dihydrogenphosphate, raffinose, glutathione, allopurinol, nafamostat mesilate and cyclodextrin, and the especially preferred organ storage solution or perfusate of the present invention is characterized by having the composition of 100–120 mM sodium lactobionate, 25–35 mM sodium dihydrogenphosphate, 25–35 mM raffinose, 2–4 mM glutathione, 1–2 mM allopurionol, 0.5–1 mM nafamostat mesilate, an osmotic pressure of 290–350 mOsm/l and a pH of 7.0–8.0.

Examples of the present invention are shown below, but it is to be understood that the present invention is not limited by these examples.

EXAMPLE 1

41.8 g of sodium lactobionate, 3.00 g of sodium dihydrogenphosphate, 15.13 g of raffinose, 0.92 g of glutathione and 0.14 g of allopurinol were added and dissolved in approximately 800 ml of distilled water (solution A). Separately from the above, 0.43 g of nafamostat mesilate was added and dissolved in 100 ml of distilled water (solution B). Solution A and solution B were mixed, then distilled water was added to make the total amount of the solution 1,000 ml, and the mixed solution was filtered and sterilized.

EXAMPLE 2

41.8 g of sodium lactobionate, 3.00 g of sodium dihydrogenphosphate, 15.13 g of raffinose, 0.92 g of glutathione, 0.14 g of allopurinol, 3.4 g of β-cyclodextrin and 13 g of γ-cyclodextrin were added and dissolved in 800 ml of distilled water (solution A). Separately from the above, 0.43 g of nafamostat mesilate was added and dissolved in 100 ml of distilled water (solution B). Solution A and solution B were mixed, then distilled water was added to make the total amount of the solution 1,000 ml, and the mixed solution was filtered and sterilized.

The stability test conducted on the formulation of Example 1 and the formulation of Example 2 is shown in Test Example 1. The organ transplantation tests carried out with the formulation of Example 1 are shown in Test Example 2 and Test Example 3.

TEST EXAMPLE 1

Compositional interaction of the formulations of Examples 1 and 2 are shown in Table 1. The figures indicate persistence (%) of nafamostat mesilate. As is evident from Table 1, in case cyclodextrin was added, precipitation was obviously suppressed and no compositional interaction took place.

TABLE 1

| | Compositional interaction test | | | | |
| --- | --- | --- | --- | --- | --- |
| Time (h) | 0 | 3 | 24 | 48 | 72 |
| Formulation of Example 1 Appearance | Sedimentation | Sedimentation | Sedimentation | Sedimentation | Sedimentation |
| Persistence | 100 | 45.5 | 20.2 | 19.7 | 15.2 |
| Formulation of Example 2 Appearance | clear solution | clear solution | clear solution | clear solution | clear solution |
| Persistence | 100 | 100 | 98 | 68.3 | 56.4 |

The test results obtained when rat organs were preserved by using a storage solution (Example 1) of the present invention and a conventional storage solution are shown below.

TEST EXAMPLE 2

Male rats with body weight of 150–250 g were used as test animals. 65 mg/kg of streptozocin was intravenously injected to the rats, and those of the rats whose blood-sugar level elevated to and stayed at 300 mg/ml or higher for more than 3 days were used as diabetic rats (recipients). Cuff technique was used as pancreas transplanting technique, and syngeneic pancreas was transplanted to the cervical region.

In the test groups, the extirpated pancreas was preserved in UW solution for 48 hours or 72 hours and perfused by using a physiological saline or a storage solution of the present invention, or the extirpated pancreas was preserved in a storage solution of the present invention for 72 hours and perfused with a storage solution of the present invention. The take rate of the transplanted organ is shown in Table 2.

TABLE 2

Effect of various types of storage solution and perfusate in rat pancreas transplantation

| | | Take rate of transplanted organ | |
| --- | --- | --- | --- |
| Storage solution | Perfusate | Preserved for 48 hours | Preserved for 72 hours |
| UW solution | Physiological saline | 44% | 0% |
| | Carolina Rinse solution | 63% | 0% |
| | Storage solution of this invention (Example 1) | 100% | 56% |
| Storage solution of this invention (Example 1) | Storage solution of this invention (Example 1) | 100% | 80% |

As is apparent from Table 2, when perfusion was carried out with a storage solution of the present invention, it was possible to preserve the organ for a longer period of time than when perfusion was carried out with a physiological saline or Caroline Rinse solution. Further, the organ could be preserved for the longest period of time when organ storage and perfusion were carried out by using a storage solution of the present invention.

TEST EXAMPLE 3

Using male rats with body weight of 150–250 g as test animals and employing Cuff technique as heart transplanting technique, syngeneic heart was transplanted to the cervical region.

In the test groups, the extirpated heart was preserved in UW solution for 18 hours and perfused with a physiological saline, Caroline Rinse solution or a storage solution of the present invention, or the extirpated heart was preserved in a storage solution of the present invention for 18 hours and perfused with a storage solution of the present invention. The take rate of the transplanted organ is shown in Table 3.

TABLE 3

Effect of various types of storage solution and perfusate in rat heart transplantation

| Storage solution | Perfusate | Take rate of transplanted organ |
| --- | --- | --- |
| UW solution | Physiological saline | 50% |
| | Carolina Rinse solution | 50% |
| | Storage solution of this invention (Example 1) | 100% |
| Storage solution of this invention (Example 1) | Storage solution of this invention (Example 1) | 100% |

As is apparent from Table 3, when perfusion was carried out with a storage solution of the present invention, the take rate of the transplanted organ was better than when perfusation was conducted with a physiological saline or Carolina Rinse solution. Further, good results were obtained when organ storage and perfusion were carried out with a storage solution of the present invention.

What is claimed is:

1. A solution for the preservation or perfusion of an organ consisting essentially of sodium lactobionate, sodium dihydrogenphosphate, raffinose, glutathione, allopurinol and nafamostat mesilate in concentrations effective for organ preservation or perfusion.

2. The solution according to claim 1 wherein the concentration of sodium lactobionate is 100–120 mM, sodium dihydrogenphosphate is 25–35 mM, raffinose is 25–35 mM, glutathione is 2–4 mM, allopurinol is 1–2 mM, nafamostat mesilate is 0.5–1 mM and the solution provides an osmotic pressure of 290–350 mOsm/l and has a pH of 7.0–8.0.

3. The solution according to claim 1, said solution consisting of sodium lactobionate, sodium dihydrogenphosphate, raffinose, glutathione, allopurinol and nafamostat mesilate in concentrations effective for organ preservation or perfusion.

4. A solution for the preservation or perfusion of an organ consisting essentially of sodium lactobionate, sodium dihydrogenphosphate, raffinose, glutathione, allopurinol, nafamostat mesilate and cyclodextrin in concentrations effective for organ preservation or perfusion.

5. The solution according to claim 4 wherein the concentration of sodium lactobionate is 100–120 mM, sodium dihydrogenphosphate is 25–35 mM, raffinose is 25–35 mM, glutathione is 2–4 mM, allopurinol is 1–2 mM, nafamostat mesilate is 0.5–1 mM, cyclodextrin is 3–30 mM and the solution provides an osmotic pressure of 290–350 mOsm/l and has a pH of 7.0–8.0.

6. The solution according to claim 4, said solution consisting of sodium lactobionate, sodium dihydrogenphosphate, raffinose, glutathione, allopurinol, nafamostat mesilate and cyclodextrin in concentrations effective for organ preservation or perfusion.

7. The solution according to claim 4 wherein said cyclodextrin is selected from the group consisting of α-cyclodextrin, β-cyclodextrin, γ-cyclodextrin, and mixtures thereof.

8. A method for preserving or perfusing organs comprising contacting an organ with a solution according to claim 1 or 3 in an amount sufficient to preserve or perfuse the organ.

9. The method according to claim 8 further comprising storing the organ in said solution.

10. The method according to claim 8 wherein the solution is the solution of claim 3.

11. The method according to claim 10 wherein said cyclodextrin is selected from the group consisting of α-cyclodextrin, β-cyclodextrin, γ-cyclodextrin, and mixtures thereof.

12. The method according to claim 5 or 10 wherein the concentration of sodium lactobionate is 100–120 mM.

13. The method of claim 8 or 10 wherein the concentration of sodium dihydrogenphosphate is 25–35 mM.

14. The method of claim 8 or 10 wherein the concentration of raffinose is 25–35 mM.

15. The method of claim 8 or 10 wherein the concentration of glutathione is 2–4 mM.

16. The method of claim 8 or 10 wherein the concentration of allopurinol is 1–2 mM.

17. The method of claim 10 wherein the cyclodextrin is 0.5–1 mM.

* * * * *